United States Patent
Augustine et al.

(10) Patent No.: US 6,558,413 B2
(45) Date of Patent: *May 6, 2003

(54) INFLATABLE DEVICE WITH EXHAUSTING APERTURES WHICH VARY IN DENSITY

(75) Inventors: Scott D. Augustine, Blue Springs, MO (US); Douglas J. Augustine, Blue Springs, MO (US)

(73) Assignee: Augustine Medical, Inc., Eden Prairie, MN (US)

( * ) Notice: Subject to any disclaimer, the term of this patent is extended or adjusted under 35 U.S.C. 154(b) by 82 days.

This patent is subject to a terminal disclaimer.

(21) Appl. No.: 09/802,642

(22) Filed: Mar. 9, 2001

(65) Prior Publication Data

US 2001/0041922 A1 Nov. 15, 2001

Related U.S. Application Data

(63) Continuation of application No. 08/846,089, filed on May 16, 1997, which is a continuation of application No. 08/658,315, filed on Jun. 5, 1996, now abandoned, which is a continuation of application No. 08/386,324, filed on Feb. 10, 1995, now abandoned, which is a continuation of application No. 08/225,141, filed on Apr. 8, 1994, now abandoned, which is a continuation of application No. 07/703,592, filed on May 20, 1991, now Pat. No. 5,324,320.

(51) Int. Cl.[7] .................................................. A61F 7/00
(52) U.S. Cl. ..................................................... 607/107
(58) Field of Search .............................. 607/104–107; 165/46; 62/259.3; 5/482, 485

(56) References Cited

U.S. PATENT DOCUMENTS

| | | | |
|---|---|---|---|
| 222,690 A | 12/1879 | Goldschmidt | ............... 128/403 |
| 1,399,095 A | 12/1921 | Webb, Sr. | .................... 128/402 |
| 1,777,982 A | 10/1930 | Popp | .......................... 128/399 |
| 2,093,834 A | 9/1937 | Gaugler | ....................... 128/402 |

(List continued on next page.)

FOREIGN PATENT DOCUMENTS

| | | | |
|---|---|---|---|
| DE | 3308553 | 3/1983 | ............. A61F/7/00 |
| DE | 0 113 420 | 11/1983 | |
| EP | 88309191.0 | 10/1988 | ............. A61F/7/10 |
| GB | 716746 | 10/1954 | |
| GB | 1 334 935 | 10/1973 | |
| GB | 1 461 383 | 1/1977 | |
| GB | 1 532 219 | 11/1978 | |
| GB | 1 566 207 | 4/1980 | |

OTHER PUBLICATIONS

Search Report in EPO Patent Application EPO 88309191.0.
*Augustine Medical, Inc. v. Gaymar Industries, Inc.*, 50 USPQ2d 1900 (CAFC 1999).

(List continued on next page.)

*Primary Examiner*—Mark S. Graham
(74) *Attorney, Agent, or Firm*—Gray Cary Ware & Freidenrich; Terrance A. Meador

(57) ABSTRACT

An inflatable cover is constructed with a base sheet to which is attached an overlaying material sheet in order to form an inflatable structure. There is an opening to admit warmed air into the inflatable structure. A plurality of apertures open through the base sheet, into the inflatable structure for the purpose of exhausting warmed air therefrom, through the base sheet. The plurality of apertures vary in density toward an edge of the base sheet for the purpose of establishing various temperature profiles with respect to the inflatable cover. In a particular embodiment, the density of the apertures increases toward the edges of the base sheet, from the center of the inflatable cover.

13 Claims, 2 Drawing Sheets

U.S. PATENT DOCUMENTS

| | | | | |
|---|---|---|---|---|
| 2,110,022 A | * | 3/1938 | Kliesrath | 607/104 |
| 2,122,964 A | | 7/1938 | Sweetland | 34/26 |
| 2,512,559 A | | 6/1950 | Williams | 5/347 |
| 2,601,189 A | | 6/1952 | Wales, Jr. | 4/160 |
| 2,706,988 A | | 4/1955 | Weber | 128/402 |
| 3,418,726 A | | 12/1968 | Sparks | 34/99 |
| 3,610,251 A | | 10/1971 | Sanderson | 128/379 |
| 3,610,323 A | | 10/1971 | Troyer | 165/46 |
| 3,691,646 A | | 9/1972 | Ruffolo | 34/99 |
| 3,714,947 A | | 2/1973 | Hardy | 128/400 |
| 3,757,366 A | | 9/1973 | Sacher | 5/347 |
| 4,572,188 A | * | 2/1986 | Augustine | 607/107 |
| 4,660,388 A | | 4/1987 | Greene | 5/485 |
| 4,777,802 A | | 10/1988 | Feher | 62/3 |
| 4,867,230 A | | 9/1989 | Voss | 165/46 |
| 5,125,238 A | | 6/1992 | Ragan et al. | |
| 5,184,612 A | * | 2/1993 | Augustine | 607/107 |
| 5,246,656 A | | 9/1993 | Stephenson et al. | 264/153 |
| 5,300,100 A | | 4/1994 | Hickle et al. | 607/107 |
| 5,300,101 A | | 4/1994 | Augustine et al. | |
| 5,300,102 A | | 4/1994 | Augustine et al. | |
| 5,324,320 A | | 6/1994 | Augustine et al. | |
| 5,336,250 A | | 8/1994 | Augustine | |
| 5,343,579 A | | 9/1994 | Dickerhoff et al. | |
| 5,360,439 A | | 11/1994 | Dickerhoff et al. | 607/104 |
| 5,384,924 A | | 1/1995 | Dickerhoff et al. | 5/421 |
| 5,443,488 A | | 8/1995 | Namenye et al. | |

OTHER PUBLICATIONS

Augustine Medical, Inc. Bair Hugger® Blanket—*Therapy Model 300 Full Body* (1 blanket).

Heinz Massinger, *Langenscheidt's New College German Dictionary*, pp. 327 & 357, New Edition 1973.

Ninth New Collegiate Dictionary, regarding laminate.

Webster's Third New International Dictionary, p. 250, regarding bond.

McGraw–Hill Encyclopedia of Science & Technology, 7th Edition, p. 713, regarding bonding.

\* cited by examiner

INFLATABLE DEVICE WITH EXHAUSTING APERTURES WHICH VARY IN DENSITY

This is a continuation of U.S. patent application Ser. No. 08/846,089, filed May 16, 1997, entitled THERMAL BLANKET which is a continuation of Ser. No. 08/658,315, filed Jun. 5, 1996, abandoned, which is a continuation of Ser. No. 08/386,324, filed Feb. 10, 1995, abandoned, which is a continuation of Ser. No. 08/225,141 Apr. 4, 1994 abondoned, which is a continuction of Ser. No. 07/703,592, filed May 20, 1991, now U.S. Pat. No. 5,324,320.

BACKGROUND OF THE INVENTION

This invention relates to thermal blankets used in a medical setting to deliver a bath of a thermally-controlled medium to a patient.

The thermal blanket prior art is best expressed in our prior U.S. Pat. No. 4,572,188 entitled "AIRFLOW COVER FOR CONTROLLING BODY TEMPERATURE." In our prior patent, a self-erecting, inflatable airflow cover is inflated by the introduction into the cover of a thermally-controlled inflating medium, such as warmed air. When inflated, the cover self-erects about a patient, thereby creating an ambient environment about the patient, the thermal characteristics of which are determined by the temperature of the inflating medium. Holes on the underside of our prior art airflow cover exhaust the thermally-controlled, inflating medium from inside the cover to the interior of the erected structure. Our airflow cover is intended for the treatment of hypothermia, as might occur post-operatively.

Evaluation of our airflow cover by skilled practitioners has resulted in general approbation: the opinion is that the airflow cover efficiently and effectively accomplishes its purpose of giving a thermally-controlled bath. We have realized, however, that, while our prior art airflow cover achieves its objective, certain improvements to it are necessary in order to realize additional clinical objectives and to enjoy further advantages in its use.

SUMMARY OF THE INVENTION

We have improved the clinical usefulness of our self-erecting airflow cover by observing that controlling the contour of its inflatable portion at its head end to define a generally concave non-inflatable portion will permit a care giver to more easily observe a patient's head, face, neck and chest. Further, we have observed that limited venting of the thermally controlled inflating medium from the edges of the cover results in more efficient, more uniform heating within the cover. We have also observed that it is good clinical practice to keep the area of the care site in the vicinity of the patient's head and face as clean as possible.

These three observations have resulted in an improved thermal blanket in which a self-erecting inflatable covering has a head end, a foot end, two edges, and an undersurface. An inflating inlet adjacent said foot end admits a thermally-controlled inflating medium into the covering. An aperture array on the undersurface of the covering exhausts the thermally-controlled inflating medium from the covering into the structure created when the covering self-erects upon inflation. The improvements to this basic structural complement include an uninflatable section at the head end of the covering, exhaust port openings at the edges of the covering, an absorbent bib attached to the covering at the head end adjacent the uninflatable section, and structural features that make the covering simple and economical to produce.

With these improvements, the thermal blanket, when inflated and erected over a patient, delivers the thermally-controlled inflating medium into the interior of the structure covering the patient, thereby thermally bathing the patient. The first improvement permits full viewing of the head and face of the patient from almost any aspect around the thermal blanket. The exhaust port openings increase the rate of circulation of the inflating medium within the blanket, thereby increasing the temperature within the structure and making the temperature distribution more uniform. The absorbent bib soaks up and retains liquids which might otherwise spread over the care site in the area of a patient's head. Such liquids can include the patient's own perspiration, blood, vomit, saliva, or liquids which are administered to the patient. The absorbent bib also acts to some extent to seal the head end of the inflated structure.

From another aspect, the invention is a thermal blanket for covering and bathing a person in a thermally-controlled medium. The thermal blanket includes a flexible base sheet having a head end, a foot end, two edges, and a plurality of apertures opening between the first and second surface of the base sheet. An overlying material sheet is attached to the first surface of the base sheet by a plurality of discontinuous seams which form the material sheet into a plurality of substantially parallel, inflatable chambers. A continuous seam is provided between the material sheet and the base sheet at the head end to form a non-inflatable viewing recess at the head end. Exhaust port openings are provided through the material sheet to vent the medium from the chambers away from the base sheet. An absorbent bib is attached to the head end in the vicinity of the viewing recess.

Therefore the invention accomplishes the important objective of providing a self-erecting, inflatable thermal blanket that permits a relatively unobstructed view of a patient's head and face when in use.

Another objective is the efficient and uniform heating of the interior of the structure created when the blanket is inflated with a heat inflating medium.

A signal advantage of the invention is the provision of such a blanket with a means for maintaining the cleanliness of the care site in the vicinity of the patient's head and face.

The advantageous simplified structure of the thermal blanket make its production straightforward and economical.

These and other important objectives and advantages will become evident when the detailed description of the invention is read with reference to the below-summarized drawings, in which.

DETAILED DESCRIPTION OF THE PREFERRED EMBODIMENT

When used herein, the term "thermal blanket" is intended to be interchangeable with, but not necessarily limited by, the term "airflow cover" used in our U.S. Pat. No. 4,572,188, which is incorporated herein in its entirety by reference. In this description, the term "thermal blanket" is meant to invoke a self-erecting, inflatable structure for delivering a thermally-controlled inflating medium to the interior of the structure created when the thermal blanket is inflated. The purpose of the thermal blanket is to efficiently administer a uniformly thermally-controlled bath of the inflating medium to a patient within the erected structure.

Figure 1:
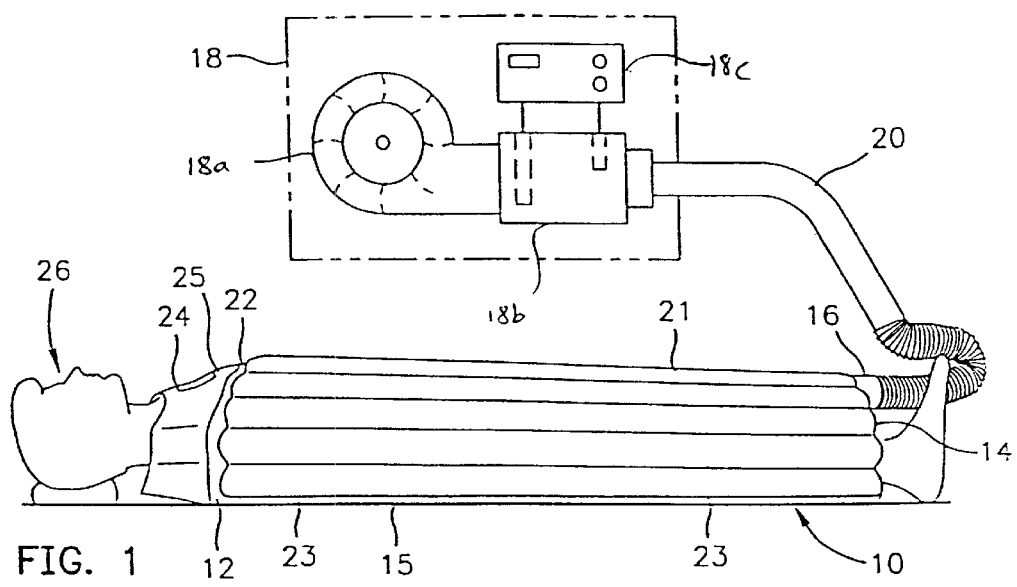
FIG. 1 is a side elevation view of the thermal blanket in use, with associated thermal apparatus indicated schematically.

Our invention is illustrated as we intend for it to be used in FIG. 1. In FIG. 1, a self-erecting, inflatable thermal blanket 10 has a head end 12, a foot end 14 and two lateral edges, one indicated by 15. An inflation inlet cuff 16 is connected to a heater/blower assembly 18 which provides a stream of heated air through a connecting hose 20. When the heater/blower 18 is operated, the stream of heated air flows through the inflating hose 20 into the thermal blanket 10 through the inflation cuff 16. When the blanket is inflated, it erects itself into a Quonset hut-like structure with a quilted upper surface 21. As described below, a pattern of apertures on the undersurface of the blanket (not shown in FIG. 1) delivers the inflating heated air into the interior space enclosed by the erected thermal blanket.

The contour of the inflatable portion of the thermal blanket 10 is varied at the head end 12 of the blanket to provide a non-inflated blanket recess 22 in the quilted upper surface 21, which remains smooth and flat when the blanket is inflated and erected. Circulation of the heated air is accelerated through the thermal blanket by exhaust port openings in the upper surface, adjacent the lateral edges of the blanket. Two exhaust port openings are indicated by reference numeral 23. Further, a bib 24 made of an absorbent material is attached to the head end 12 of the thermal blanket in the vicinity of the non-inflated recess 22. In fact, as shown in FIG. 1, the bib 24 includes a semi-circular tab 25 that extends into the recess 22.

As illustrated in FIG. 1, the thermal blanket of the invention is inflated, erects itself into a bathing structure, and bathes a patient 26 with the thermally-controlled air used to inflate the structure. While the patient is being thermally bathed, the uninflated recess 22 permits observation of the patient's head, face, neck, and chest from almost any location with respect to the thermal blanket 10. Thus, if the patient is placed on a gurney or a bed, the head of which is against a wall, a care giver such as a nurse, intern, resident, or doctor, can keep the patient's face under observation from the foot end 14 of the thermal blanket 10. Respiration can be detected by the rise and fall of the bib and uninflated area, which rest directly on the patient's chest. Moreover, the bib 24 will provide an absorbent sink for stray, unconfined liquids in the area of the patient's head or at the head end 12 of the thermal blanket 10.

Figure 2:
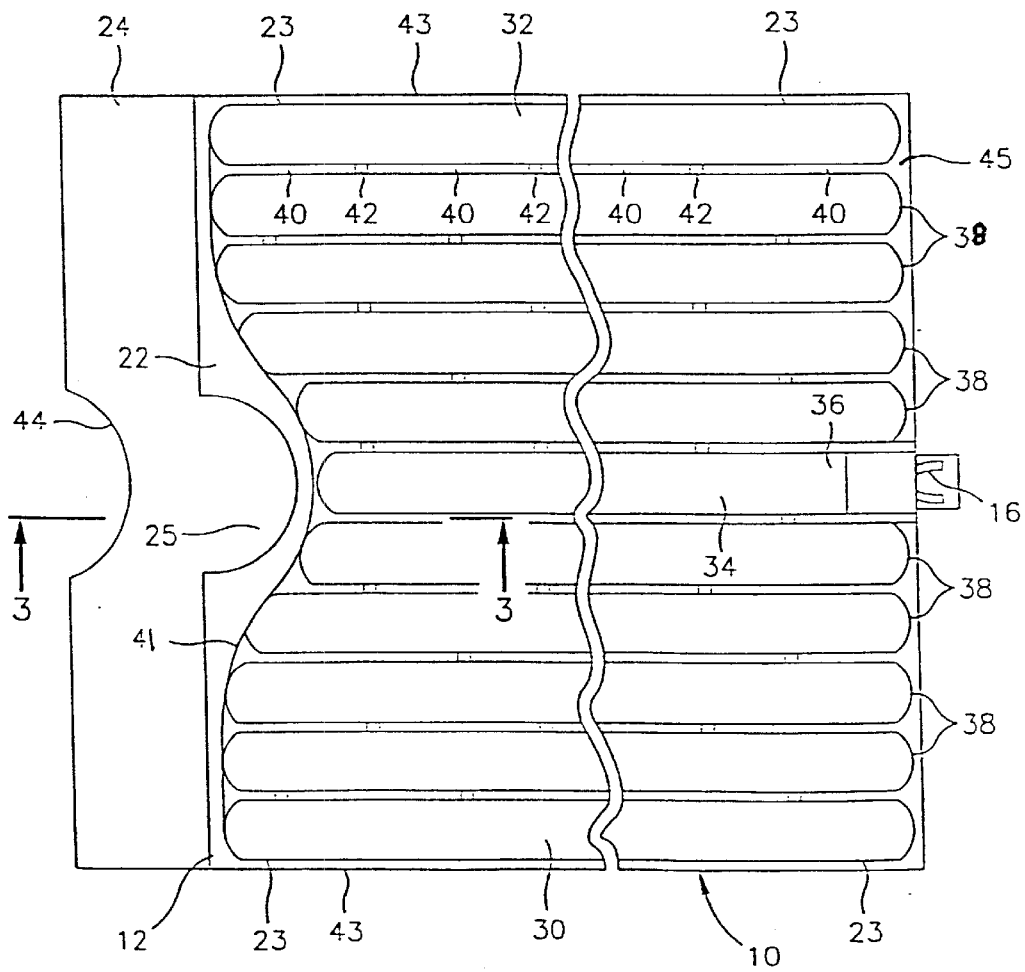
FIG. 2 is an enlarged top plan view of the thermal blanket opened flat.

FIG. 2 is a plan view of the thermal blanket 10 opened flat to show details of its structure. FIG. 2 illustrates the upper surface of the thermal blanket, that is the side that is visible in FIG. 1. As seen, the upper surface consists of a parallel array of elongated tubes of which 30 and 32 are the lateralmost tubes, 34 is the center tube, and the tubes 38 are arrayed between one of the lateralmost tubes and the center tube. Each tube is separated from an adjacent tube by a discontinuous seam, one of which is indicated by 40. The seam 40 separates the tube 32 and its nearest adjacent neighbor 38. The discontinuous seam 40 is interrupted by passageways 42 communicating between the tubes. An interrupted seam separates every tube from one adjacent neighboring tube. The seams permit the thermal blanket, when inflated, to assume a tubular structure on the upper surface, while the ports 42 permit full circulation of the inflating medium throughout the array of tubes. The foot-end seam 45 is continuous. The tubes are inflated through the center tube 34 which transitions to a port 36, through which the inflation cuff 16 is inserted. The edge seams 43 are discontinuous only at the exhaust port opening locations 23. A seal can be made between the inflation port 36 and the inflation cuff 16 by any conventional means, for example, an O-ring, or even tape. When the inflating medium is introduced into the center tube 34, it flows laterally from the center tube into all of the other tubes through the ports 42. Near the head end 12, a continuous seam 40 defines the forward end of all of the tubes, with the seam assuming a bell-curve shape. On the head end side of the seam 40, the thermal blanket 10 is uninflatable. The bell-shaped seam 40 thus defines the uninflatable area 22 at the head end of the thermal blanket 10, which is essentially coplanar with, or substantially parallel to, the underside of the blanket. As shown in FIG. 1, by virtue of its structural integration with the rest of the thermal blanket 10, the non-inflated recess extends over the upper chest of the patient 26 when the blanket is inflated. However, since the recess 22 is uninflated, it provides a wide-angled viewing gap in the inflated contour of the upper surface 21. The gap is filled by continuation of the underside of the blanket. It is also noted that the pattern of inflatable tubes can be replaced by other suitable patterns of communicating, inflatable chambers. The tubes are preferred since they impart strength and shape to the erected bathing structure; other inflatable structures are contemplated, however.

The absorbent bib has an indent 43 cut into its outside edge, which permits the blanket to be drawn up to the chin of a patient and which provides absorbency laterally up the neck of the patient. The absorbent bib can consist of any absorbent material such as a single- or multi-ply tissue paper which is used to make paper towels.

Figure 3:
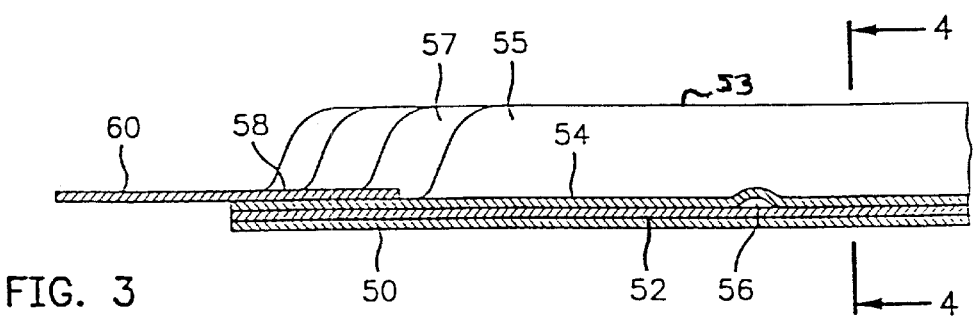
FIG. 3 is an enlarged sectional view taken along 3—3 of FIG. 2.
Figure 4:
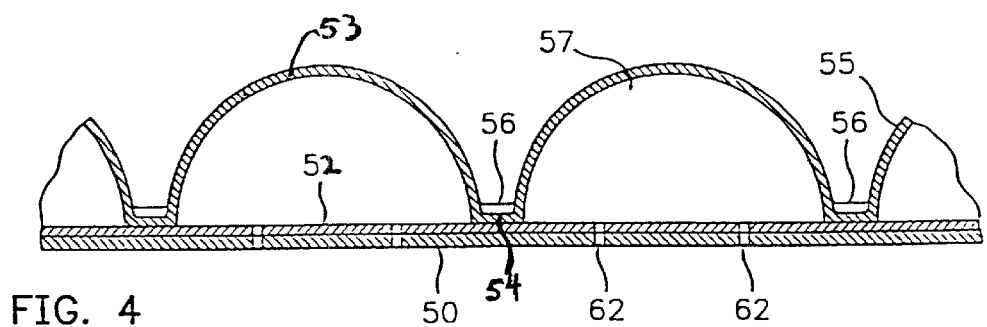
FIG. 4 is a further enlarged sectional view taken along line 4—4 of FIG. 3.

Construction details of the thermal blanket 10 are illustrated in FIGS. 3 and 4. The thermal blanket 10 is assembled from a base sheet consisting of an underside layer 50 formed from flexible material capable of bonding to a layer 52 of heat-sealable plastic. For the layers 50 and 52, we have used a stratum of absorbent tissue paper prelaminated with a layer of heat-sealable plastic. Material of such construction is commercially available in production rolls and is used to make painters' drop cloths. The upper side of the thermal blanket consists of a sheet of plastic bonded to the plastic layer 52 by an interruptible heat-sealing process to form the interrupted seams, one of which is indicated by 54, and the inflatable tubes, one indicated by 55. As can be seen in FIG. 3, the interruption of the seam 54 forms a passageway 56 between adjacent tubes 55 and 57.

The absorbent bib and tab are shown in FIG. 3 as a single material layer 60/58. Alternatively, they may be formed from separate material sheets cut to the outlines illustrated in FIG. 2. The absorbent material forming the bib and tab can be bonded to the upper plastic layer by heat process or by gluing.

The inventors also contemplate deletion of the bib and tab. In this instance, the thermal blanket would still have the viewing recess, which would be defined by the continuous seam at the head end, and which would be filled with the forward portion of the base sheet.

Circulation of heated air through the blanket is enhanced by the exhaust port openings 23, which open through the upper plastic sheet sheet, which is heat sealed to the base of the blanket. The openings 23 vent the heated inflating air out of the outermost tubes 30 and 32, away from the underside of the blanket. Because air can circulate to, and through, the blanket edges, the inflating air in the outermost tubes is hotter than if the openings were absent. This results in hotter air being delivered through the underside apertures toward the edge of the blanket. We have measured the temperature distribution within the thermal blanket for inflating air which is heated to a medium temperature range and for inflating air which is heated to a high temperature range. The results are provided in Table I for a blanket consisting of 13 tubes. Measurements of the temperature of air exhausted through underside apertures were made on the underside of each tube on one side of the blanket. The tubes are numbered 1–6, with 1 being the tube adjacent to the center tube, and tube 6 being the outermost tube adjacent on lateral edge of the blanket. Test apertures were made in the bottom of tube 6 only for the purposes of this test. As is evident, the distribution of temperature within the erected thermal blanket is more uniform when the exhaust port openings are provided. Further, provision of the exhaust ports also increases the average temperature within the erected structure of the blanket. Clearly, the provision of exhaust port openings at the lateral edges of the blanket delivers results which one would not expect when considering the operation of our thermal blanket with no exhaust port openings.

In our preferred embodiment, the exhaust port openings are slits in the edge seams of our blanket. These slits vary in length from 1¾ to 2 inches. Each edge seam is discontinuous approximately at each corner of the blanket so that inflating air is vented away from the underside of the erected blanket. This keeps the relatively "colder" air at the blanket edges from mixing with the relatively "hotter" air exhausted into the structure through the underside apertures. The result is a "flatter" temperature profile of air within the blanket than without the vents, which raises the average temperature within the erected structure and makes the temperature distribution in the structure more uniform. Resultantly, the clinical effect of the blanket is enhanced. Heating is better controlled, and more uniform, with greater comfort to the patient.

TABLE I

| TUBE NO. | MEDIUM TEMPERATURE RANGE | | HIGH TEMPERATURE RANGE | |
|---|---|---|---|---|
| | WITHOUT EXHAUST PORTS | WITH 2" EXHAUST PORTS | WITHOUT EXHAUST PORTS | WITH 2" EXHAUST PORTS |
| center (inlet) tube | 113.3° F. | 114.1° F. | 121.3° F. | 121.3° F. |
| Tube #1 | 109.9° | 112.3° | 117.3° | 117.7° |
| Tube #2 | 105.3° | 109.8° | 113.4° | 115.0° |
| Tube #3 | 103.2° | 107.1° | 111.0° | 113.3° |
| Tube #4 | 99.9° | 104.3° | 101.4° | 108.6° |
| Tube #5 | 97.2° | 100.0° | 95.7° | 104.4° |
| Tube #6 (outermost) | 85.2° | 95.8° | 89.6° | 99.4° |
| Average temp. under cover | 103.8° | 106.7° | 108.4° | 112.5° |

Figure 5:
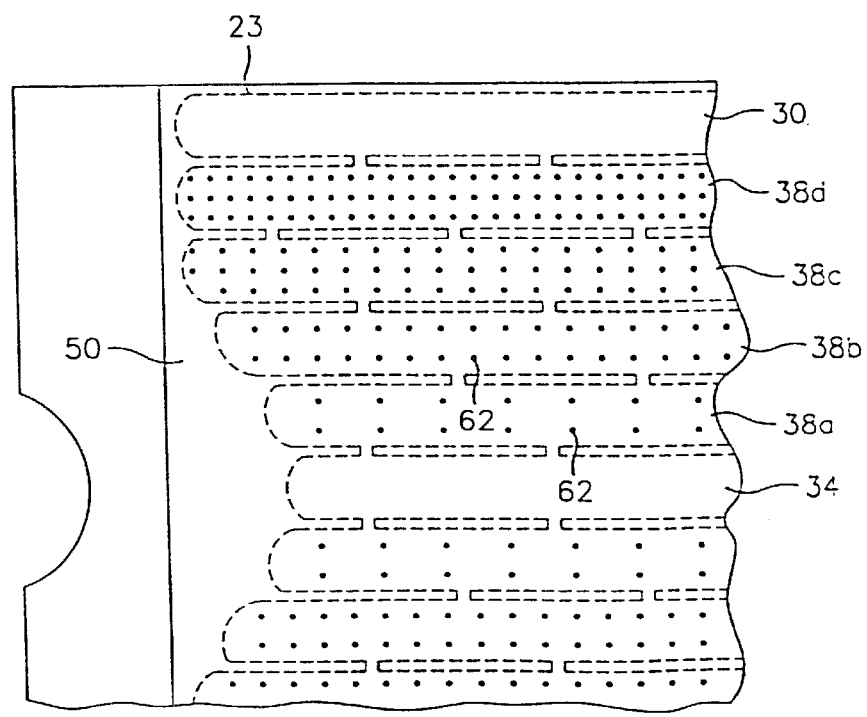
FIG. 5 is a partial underside view of the thermal blanket.

The thermal blanket of the invention is enabled to bathe a patient in the thermally-controlled inflating medium introduced into the upper side tubes by means of a plurality of apertures 62 shown in FIGS. 4 and 5. The apertures extend through the underside of the blanket, which includes the layers 50 and 52. The apertures 62 are made in the footprints of the tubes of the blanket upper side according to a pattern which has been determined to deliver a very uniform thermal bath. In this regard, no apertures are provided through the underside into the lateralmost tubes 30 and 32, or into the center tube 34. In addition, the apertures 62 are provided through the underside to the apertured tubes in a density which varies inversely with the proximity of the tube to the center tube 34. Thus, the hole density increases from the tube 38a through the tube 38d. Even with the exhaust port openings, the temperature of the inflating medium exhibits a drop from the center to the lateralmost tubes. The varying density of the apertures 62 tends to reduce this gradient further by forcing hotter air to the edges of the blanket. Thus, the thermal bath delivered to the patient is of a generally uniform temperature. The aperture density variation also equalizes the flow of inflating medium out of the apertures. As will be evident, the inflating pressure will be greatest at the center tube 34 and will tend to diminish toward the lateral edges of the thermal blanket. Therefore, fewer apertures are required for the tubes near the center tube 34 to deliver the same amount of air as the relatively greater number of apertures in the tubes at a greater distance from the center tube 34.

The apertures comprise openings which can be of any appropriate shape. For example, we have produced blankets with elongated apertures, approximately ¼ inch in length.

Many modifications and variations of our invention will be evident to those skilled in the art. It is understood that such variations may deviate from specific teachings of this description without departing from the essence of the invention, which is expressed in the following claims.

We claim:

1. An inflatable cover for convectively warming a person, comprising
   a base sheet having at least two edges;
   an overlaying material sheet attached to the base sheet at a plurality of locations to form an inflatable structure;
   an opening for admitting warmed air into the inflatable structure;
   a plurality of apertures opening through the base sheet for exhausting warmed air from the inflatable structure; and
   the plurality of apertures having a density that varies toward at least one of the edges.

2. The cover of claim 1, wherein the density of the apertures increases toward the at least one edge.

3. The cover of claim 2, wherein the density of the apertures increases from the center of the cover to the edges.

4. The cover of claim 1, wherein the opening is in the center of the inflatable structure.

5. The cover of claim 1, wherein the inflatable structure includes space between the overlaying material sheet and the base sheet.

6. The cover of claim 1, wherein the base sheet includes a first layer of a first base sheet material and a second layer of a second base sheet material laminated to the first layer.

7. The cover of claim 6, wherein the first base sheet material is a fibrous material.

8. The cover of claim 6, wherein the second base sheet material is a plastic material.

9. The cover of claim 3, wherein the inflatable structure includes a plurality of interconnecting tubes with at least one interconnecting tube near one of the edges.

10. The cover of claim 9, wherein no apertures of the plurality of apertures open through the base sheet into the interconnecting tube near the edge.

11. The cover of claims 3 or 10 wherein the inflatable structure is self-erecting.

12. The cover of claim 1, wherein the inflatable structure is self-erecting.

13. A combination for warming a person, the combination comprising: an inflatable cover for convectively warming a person, including:

a base sheet having at least two edges;

an overlaying material sheet attached to the base sheet at a plurality of locations to form an inflatable structure;

an opening for admitting warmed air into the inflatable structure;

a plurality of apertures opening through the base sheet for exhausting warmed air from the inflatable structure; and the plurality of apertures having a density that varies toward at least one of the edges an air hose having two ends;

connecting a first end of the air hose to the opening of the cover; and a heater/blower connected to a second end of the air hose.

* * * * *

UNITED STATES PATENT AND TRADEMARK OFFICE
CERTIFICATE OF CORRECTION

PATENT NO.        : 6,558,413 B2                                          Page 1 of 1
APPLICATION NO.   : 09/802642
DATED             : May 6, 2003
INVENTOR(S)       : Augustine et al.

It is certified that error appears in the above-identified patent and that said Letters Patent is hereby corrected as shown below:

Related U.S. Application Data

(63) after Pat. No. 5,324,320, add --which is a continuation of application No. 07/227,189, filed August 2, 1988, now abandoned, which is a continuation in part of application No. 07/104,682, filed October 5, 1987, now abandoned--

In the Specification

Column 1, line 11, after U.S. Patent No. 5,324,320, add --which is a continuation of U.S. Patent Application Serial No. 07/227,189, filed August 2, 1988, now abandoned, which is a continuation in part of U.S. Patent Application Serial No. 07/104,682, filed October 5, 1987, now abandoned.--

Signed and Sealed this

Fifth Day of December, 2006

JON W. DUDAS
*Director of the United States Patent and Trademark Office*